(12) United States Patent
Thoms

(10) Patent No.: US 8,334,636 B2
(45) Date of Patent: Dec. 18, 2012

(54) VIBRATION COUPLING UNIT

(76) Inventor: Michael Thoms, Bietigheim-Bissingen (DE)

( * ) Notice: Subject to any disclaimer, the term of this patent is extended or adjusted under 35 U.S.C. 154(b) by 249 days.

(21) Appl. No.: 12/594,593

(22) PCT Filed: Mar. 7, 2008

(86) PCT No.: PCT/EP2008/001816
§ 371 (c)(1),
(2), (4) Date: Feb. 12, 2010

(87) PCT Pub. No.: WO2008/119434
PCT Pub. Date: Oct. 9, 2008

(65) Prior Publication Data
US 2010/0135717 A1   Jun. 3, 2010

(30) Foreign Application Priority Data
Apr. 3, 2007   (DE) .................. 10 2007 016 353

(51) Int. Cl.
*F16B 7/00* (2006.01)
(52) U.S. Cl. ................... 310/328; 310/325; 433/119
(58) Field of Classification Search .............. 310/328, 310/325; 433/119
See application file for complete search history.

(56) References Cited

U.S. PATENT DOCUMENTS

| 3,809,977 | A | * | 5/1974 | Balamuth et al. ........... 318/116 |
| 4,012,647 | A | * | 3/1977 | Balamuth et al. ........... 310/317 |
| 4,333,197 | A | * | 6/1982 | Kuris ........................... 15/22.1 |
| 2005/0271999 | A1 | * | 12/2005 | Fishburne ..................... 433/39 |

FOREIGN PATENT DOCUMENTS

| DE | 42 38 384 | 5/1994 |
| DE | 196 41 120 | 4/1998 |
| DE | 101 21 128 | 10/2002 |
| WO | WO 2007/104470 | 9/2007 |

OTHER PUBLICATIONS

International Search Report issued in corresponding International application PCT/EP2008/001816 dated Jun. 3, 2008.

* cited by examiner

*Primary Examiner* — Walter Benson
*Assistant Examiner* — Bryan Gordon
(74) *Attorney, Agent, or Firm* — Lempia Summerfield Katz LLC

(57) ABSTRACT

The invention relates to a coupling unit (24) for transmitting high-frequency mechanical vibrations from a vibration generator (12) onto a tool (34). Said coupling unit comprises in input part (22) and an output part (30) that are interconnected via two identical vibration bars (26, 28), said bars being off-set from each other. The bars may have the shape of quadrants to provide the output movement in a direction that forms an angle of 90° with the direction of the input movement.

22 Claims, 10 Drawing Sheets

VIBRATION COUPLING UNIT

RELATED APPLICATION DATA

This U.S. national phase application is based on international application no. PCT/EP2008/001816, filed on Mar. 7, 2008, which claimed priority from German national patent application 10 2007 016 353.5 filed on Apr. 3, 2007. Priority benefit of these earlier filed applications is hereby claimed and the full disclosures of these earlier filed applications are hereby incorporated by reference herein.

BACKGROUND

1. Field of the Disclosure

The invention relates to a vibration coupling unit for transmitting mechanical vibrations from a high-frequency drive to a tool according to the pre-characterising clause of claim 1.

2. Description of the Related Art

The term "high-frequency" is intended in this instance to refer to a vibration whose frequency is between 50 Hz and 100 kHz, in particular between 15 kHz and 30 kHz.

Such a coupling unit can be seen, for example, in DE 42 38 384 A1. In this unit, the vibration system comprises a ring which vibrates transversely in resonance and in which two vibration nodes which are offset in an angular direction are connected to the input member and the output member.

Such a coupling unit operates in a satisfactory manner in many cases. However, it cannot be used to transmit the vibration energy over a relatively large distance which would sometimes be advantageous, for example, when the coupling unit is integrated in a long slim dental hand tool, by means of which rear teeth regions of a patient are intended to be treated.

SUMMARY

With the present invention, a vibration coupling unit is therefore intended to be developed according to the pre-characterising clause of claim 1 in such a manner that the transmission of the vibration energy is possible over a relatively large distance.

This object is achieved according to the invention by a vibration coupling unit having the features set out in claim 1.

The dependent claims relate to advantageous development of the invention.

A coupling unit, as set out in claim 2, substantially has the features of a parallelogram vibrator: the input movement and output movement extend in mutually parallel directions. The coupling unit also has very small dimensions in the direction perpendicular relative to the transmission direction.

The development of the invention according to claim 3 is advantageous in terms of simple production since only one type of vibration bar is required. In addition, both bars vibrate in the same manner so that there is no redirection of the output movement relative to the input movement caused by the vibration bar itself.

The development of the invention according to claim 4 also serves to achieve geometrically simple relationships and an output movement with a well-defined direction. The vibration bars form, together with the input member and output member in the non-loaded state, for example, a rectangle, and in the vibrating state, a cyclically changing parallelogram. In this manner, the input movement is further directed without changing direction. Or these components form a parallelogram or a trapezium whose corner angle changes cyclically.

The development according to claim 5 is also advantageous in terms of simple production of the vibration bars.

A coupling unit according to claim 6 can convey the vibration energy which is applied thereto over a particularly long distance, the individual vibration bars only needing to have relatively small lengths.

With the development of the invention according to claim 7, the direction of the output movement no longer corresponds to the direction of the input movement.

The development of the invention according to claim 8 allows the output movement to be kept in phase with the input movement. With the development of the invention according to claim 8, it is also possible for the driving ends of the two vibration bars to have the same identical phase position in spite of different lengths. In this manner, a linear movement which is substantially free from redirection components is again achieved at the output side.

The geometries set out in claim 9 for the vibration bars are advantageous in terms of continuous redirection of the vibration energy and compact construction of the coupling unit.

Coupling units, as set out in claim 10, are particularly suitable for the treatment of regions which are difficult to access, in particular regions of human teeth which are difficult to access.

The development of the invention according to claim 11 provides clear interfaces at the driving side of the coupling unit. The rigid construction of the input member and output member also allows the vibrations of the coupling unit to be reliably calculated in advance.

The development according to claim 12 is particularly advantageous if it is desirable to excite the coupling unit by means of a movement which is directed perpendicularly relative to the longitudinal axis thereof.

According to claim 13, it is also possible to cause the vibration bar which is remote from the drive to move.

Claim 14 allows the use of structurally mechanically simple coupling sub-units, but still allows a linear output movement to be ensured.

BRIEF DESCRIPTION OF THE DRAWINGS

The invention is explained in greater detail below by means of embodiments with reference to the drawings, in which.

DETAILED DESCRIPTION OF THE DISCLOSURE

Figure 1:
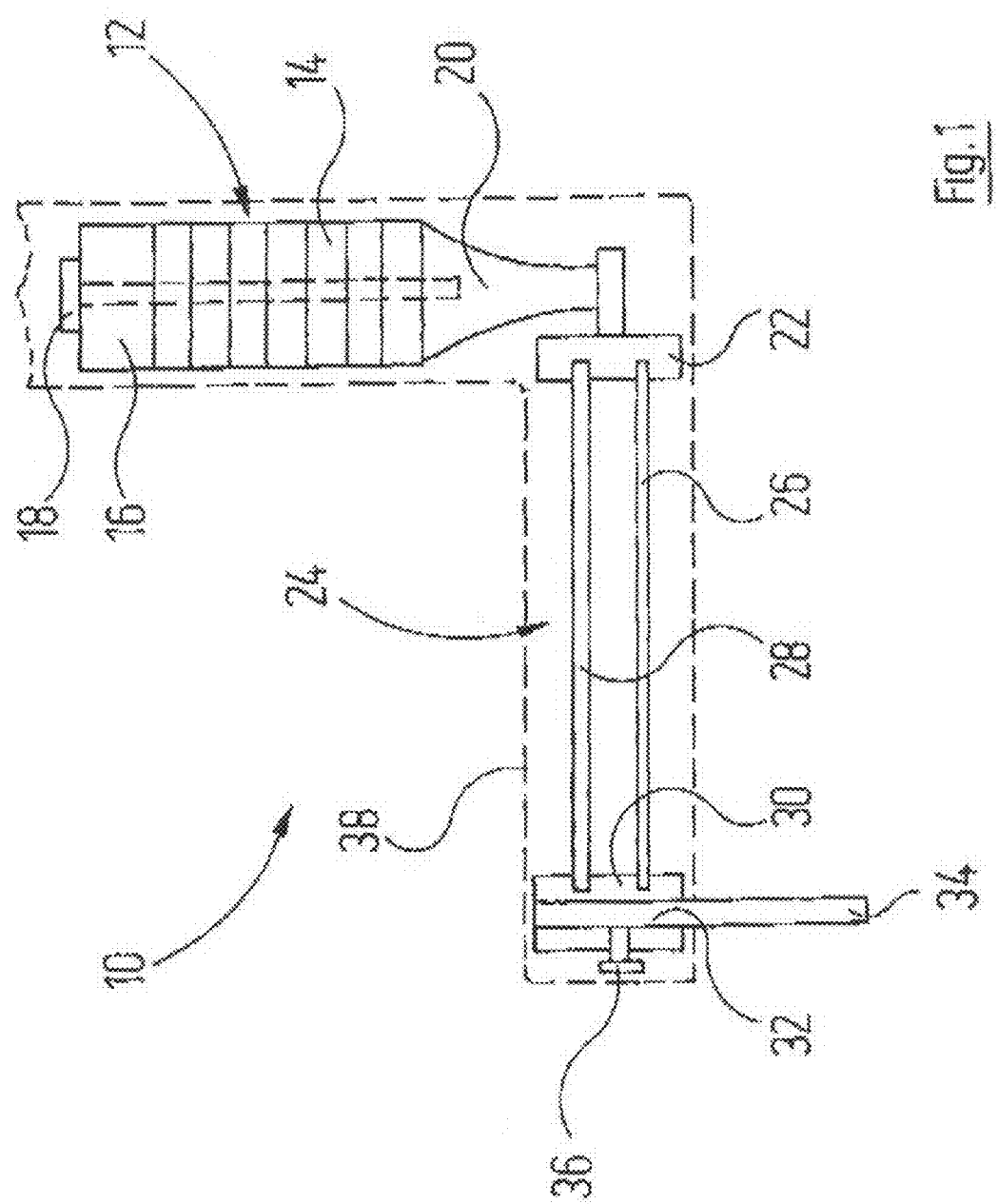
FIG. 1 is a schematic illustration of the patient portion of a dental hand tool for ultrasound treatment of tooth surfaces.

In the drawings, the patient portion of a dental hand tool which is used for ultrasound treatment of tooth surfaces and for ultrasound preparation of teeth is generally designated 10.

The ultrasound is produced by means of a vibration generator 12 which has a plurality of piezoelectric plates 14 which are stacked axially one behind the other and a counter-mass 16. The plates 14 and the counter-mass 16 are held together under tension by means of a screw 18 which is secured in the rear end of a sonotrode 20.

The ultrasound vibration produced by the vibration generator 12 when connected to an appropriate high-frequency alternating voltage source is transmitted from the sonotrode 20 to the input member 22 of a coupling unit which is generally designated 24.

The input member 22 is a parallelepipedal metal component and receives, in the left-hand lateral face thereof in FIG. 1, the driven ends of two vibration bars 26, 28.

The driving ends of the vibration bars 26, 28 which are at the left-hand side in FIG. 1 are secured in an output member 30 which can again be a parallelepipedal metal component.

The output member has a central hole 32 in which the shaft of a tool 34 is received. A screw 36 serves to fix the tool shaft in the hole 32.

The vibration generator 12 and the coupling unit 24 are surrounded with little spacing by a housing 38 which is only indicated with dashed lines in FIG. 1.

The ends of the vibration bars 26, 28 can be connected to the input member 22 and the output member by means of welding or hard-soldering.

Alternatively, the coupling unit 24 may also be constructed from a material block so that the vibration bars 26, 28 and the input member 22 and the output member 30 are also joined together in a material structure.

In order to reduce notch effects, sharp edges are rounded.

As can be seen from the drawings, the two vibration bars 26, 28 are of the same length and extend parallel with each other.

Consequently, the vibration bars 26, 28 and the input member 22 and the output member 30 define a rectangular frame which has two deformable sides (vibration bar 26, 28) and two rigid sides (input member 22 and output member 30).

The frequency of the vibration generator 12 and the inherent vibrations of the two vibration bars are coordinated in such a manner that the length of the vibration bars 26, 28 in each case corresponds to an integral multiple of a half wavelength and antinodes of the inherent vibration are located at the ends of the vibration bars.

If a vibration which is directed vertically in FIG. 1 is applied to the input member 22, the vibration bars 26, 28 are deformed in such a manner that the above-mentioned frame comprising the vibration bars 26, 28 and the input member 22 and the output member 30 is truncated and approximates to the shape of a parallelogram. After reaching an upper maximum position, the entire system then springs back. Subsequently, the system again reaches in a transient position the geometry illustrated in FIG. 1 and then springs downwards to form the shape of a parallelogram until a bottom dead centre position is reached and the parallelogram which is truncated at the bottom becomes increasingly planar again and now pivots upwards through a zero position which has the geometry illustrated in FIG. 1.

During this vibration of the vibration bars 26, 28, the output member 30 is moved in a vertical direction, and the tool 34 is also moved accordingly.

It can be seen that the movement axis of the tool is offset laterally relative to the axis of the vibration generator 12 and the sonotrode 20. In this manner, the tool 34 can operate in narrowed spaces in which there might be no space for the vibration generator 12.

Figure 2:
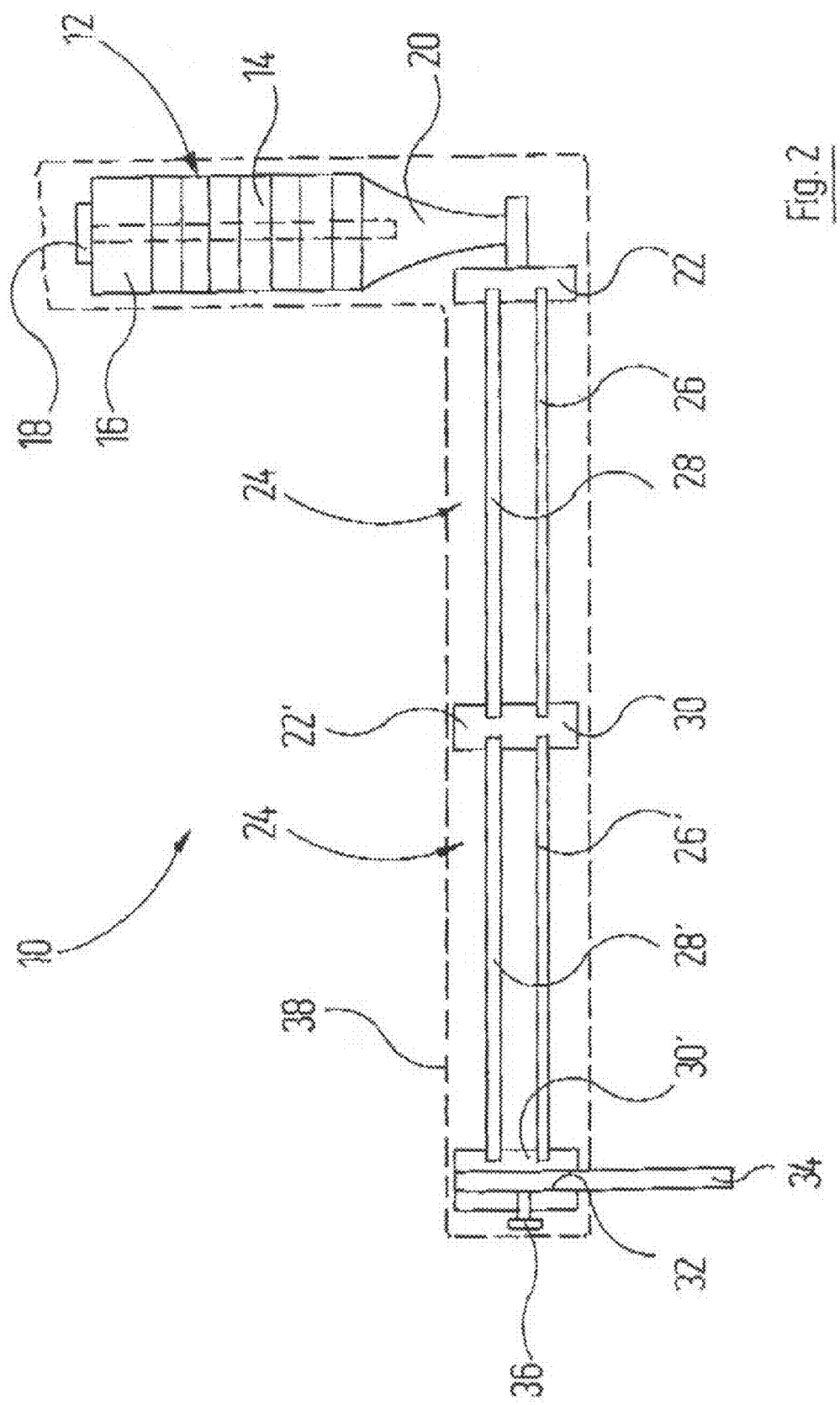
FIG. 2 is a similar view to FIG. 1, but with the trans-mission of the ultrasound energy taking place over a relatively large distance.

As can be seen in FIG. 2, the axis on which the input movement is carried out and the axis on which the tool movement is carried out can be positioned further apart by two vibration bar systems being placed one behind the other. The second one is designated by reference numerals to which a prime symbol is appended. The input member 22' of the second system is at the same time the output member 30 of the first system.

In the embodiments according to FIGS. 1 and 2, the tool movement was carried out in the same direction as the output movement of the vibration generator, but the two movement directions were offset relative to each other.

Figure 3:
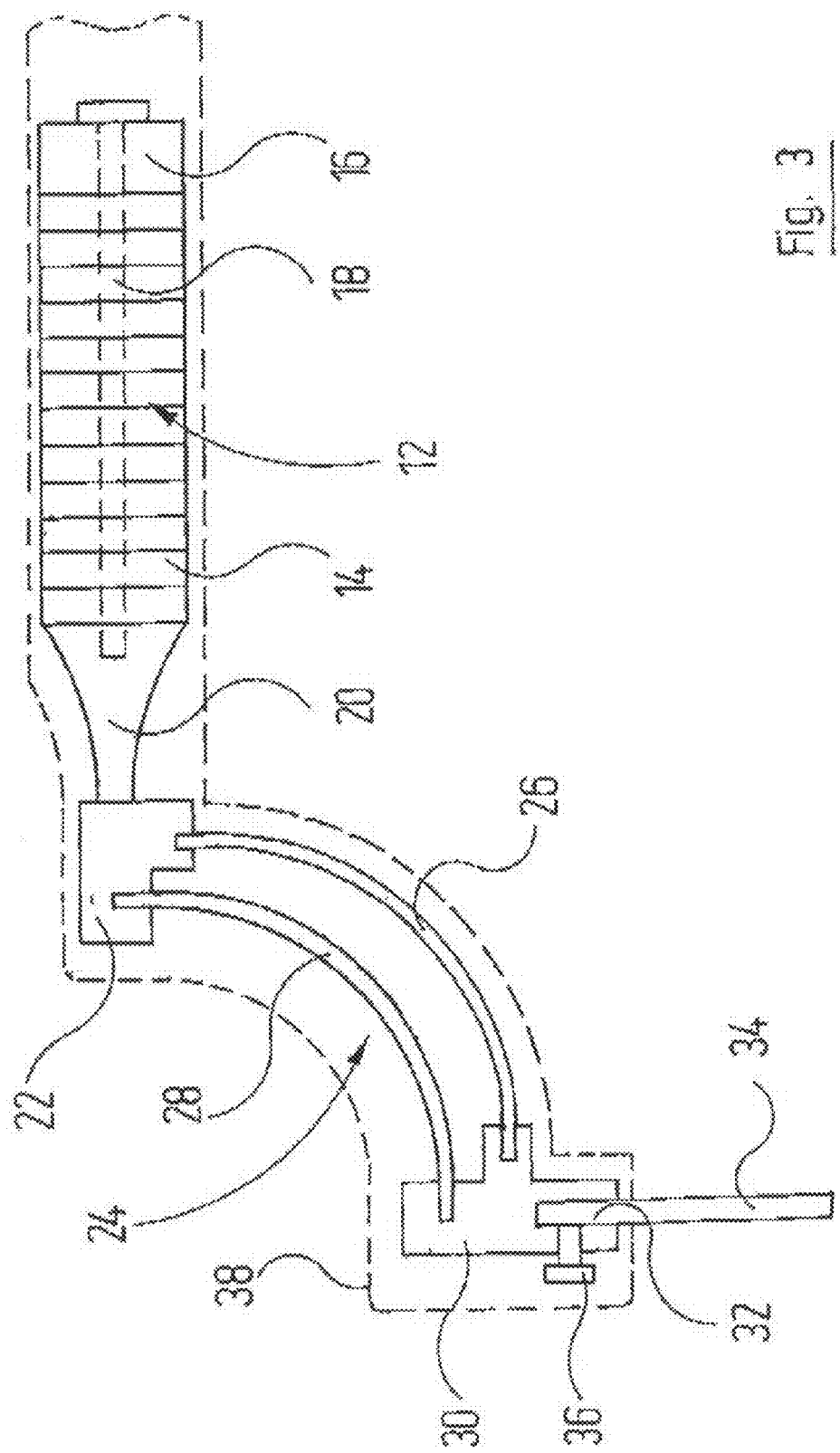
FIG. 3 is a similar view of a further modified hand tool in which a movement redirection is carried out through 90°.

In the embodiment according to FIG. 3, an angular displacement is achieved between the input movement and the output movement of the coupling unit 24. Components of the hand tool which correspond in terms of function to components already described in FIGS. 1 and 2 are again given the same reference numerals, even if they differ in terms of geometry.

The two vibration bars 26 and 28 now have the same shape of a quarter-circle. They rest with tangential end portions in the stepped input member 22 and in the stepped output member 30. Both vibration bars thus have the same length. Their centres of curvature are displaced by a fixed trans-lation relative to each other. The centres of curvature are arranged one behind the other along the axis of symmetry of the coupling unit (angle bisector between the axis of the vibration generator 12 and axis of the tool 34). Particular resistance with respect to redirection is thereby achieved.

If curved vibration bars having a different geometry (a different length, a different thickness, a different curvature) or a different material are used in a development, the parameter combinations of both vibration bars must be adapted to each other in such a manner that the in-phase excitement of the driven ends of the vibration bars 26, 28 which are located at the top in FIG. 3 also leads to an in-phase movement of the driving ends of the vibration bars 26, 28 which are located at the left-hand side in FIG. 3.

To this end, for example, the propagation rate for the vibration in a vibration bar 26 which is longer than the vibration bar 28 must be greater in accordance with the increased length of the circular arc. Such a vibration bar 26 must consequently differ from the vibration bar 28 in terms of either the material or the cross-section geometry thereof.

For the sound propagation rate in a bar, the geometrical moment of inertia thereof, the cross-section surface-area and the elasticity constant of the material are significant. Taking into account these values, the person skilled in the art is able to adapt the geometry of the two vibration bars 26, 28 to each other accordingly, whether by calculation or experiment.

The frequency of the vibration generator 12 and the inherent vibrations of the two vibration bars are again coordinated in such a manner that the length of the vibration bars 26, 28 corresponds in each case to an integral multiple of a half wavelength and antinodes of the inherent vibration are located at the ends of the vibration bars.

Figure 4:
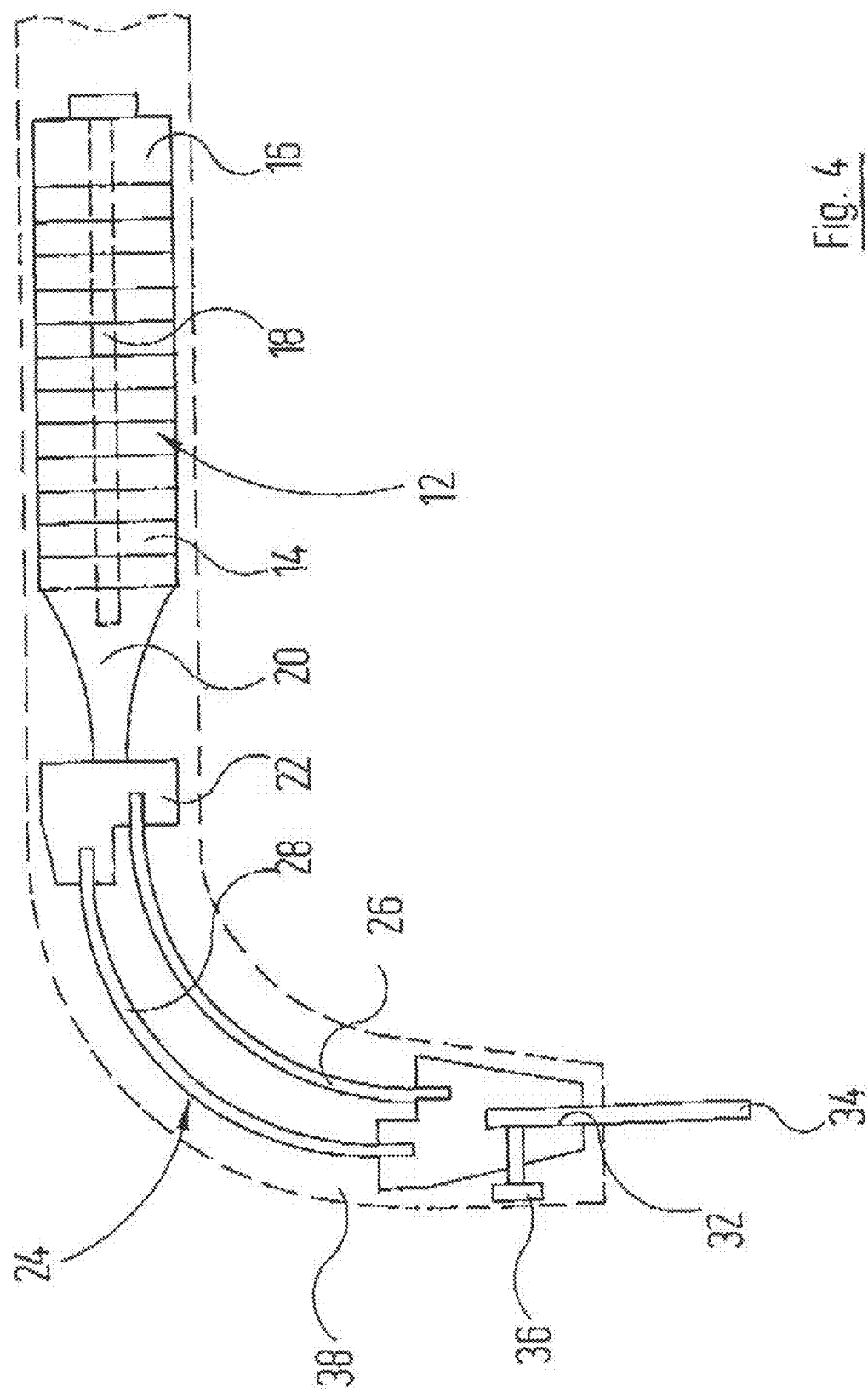
FIG. 4 is a similar view to FIG. 3, but with the coupling unit having vibration bars which are curved in the opposite direction to FIG. 3.

The embodiment according to FIG. 4 substantially corresponds to that according to FIG. 3 except that the vibration bars 22, 28 are curved in an opposing, circular manner. The embodiments of FIG. 3 apply accordingly.

In a modification of the embodiments according to FIGS. 3 and 4, the vibration bars 26, 28 may also have a different curved geometry, for example, the shape of elliptical curves, hyperbolic curves or parabolic curves. The only important aspect is that the two vibration bars 26, 28 extend in an offset manner relative to each other and the propagation rate of the ultrasound vibration is optionally different therein, and it is thus ensured that the ends of the vibration bars adjacent to the output member 30 also vibrate in an in-phase manner.

With the coupling units 24 illustrated in FIGS. 3 and 4, a tool movement is obtained in a direction which defines, with the direction of the movement produced by the vibration generator 12, an angle of 90°.

Owing to the fact that the angular extent of the vibration bars 26, 28 is selected to be smaller or larger than 90°, it is possible to modify the angle between the axis of the tool movement and the axis of the vibration generator accordingly as required and as desired.

Figure 5:
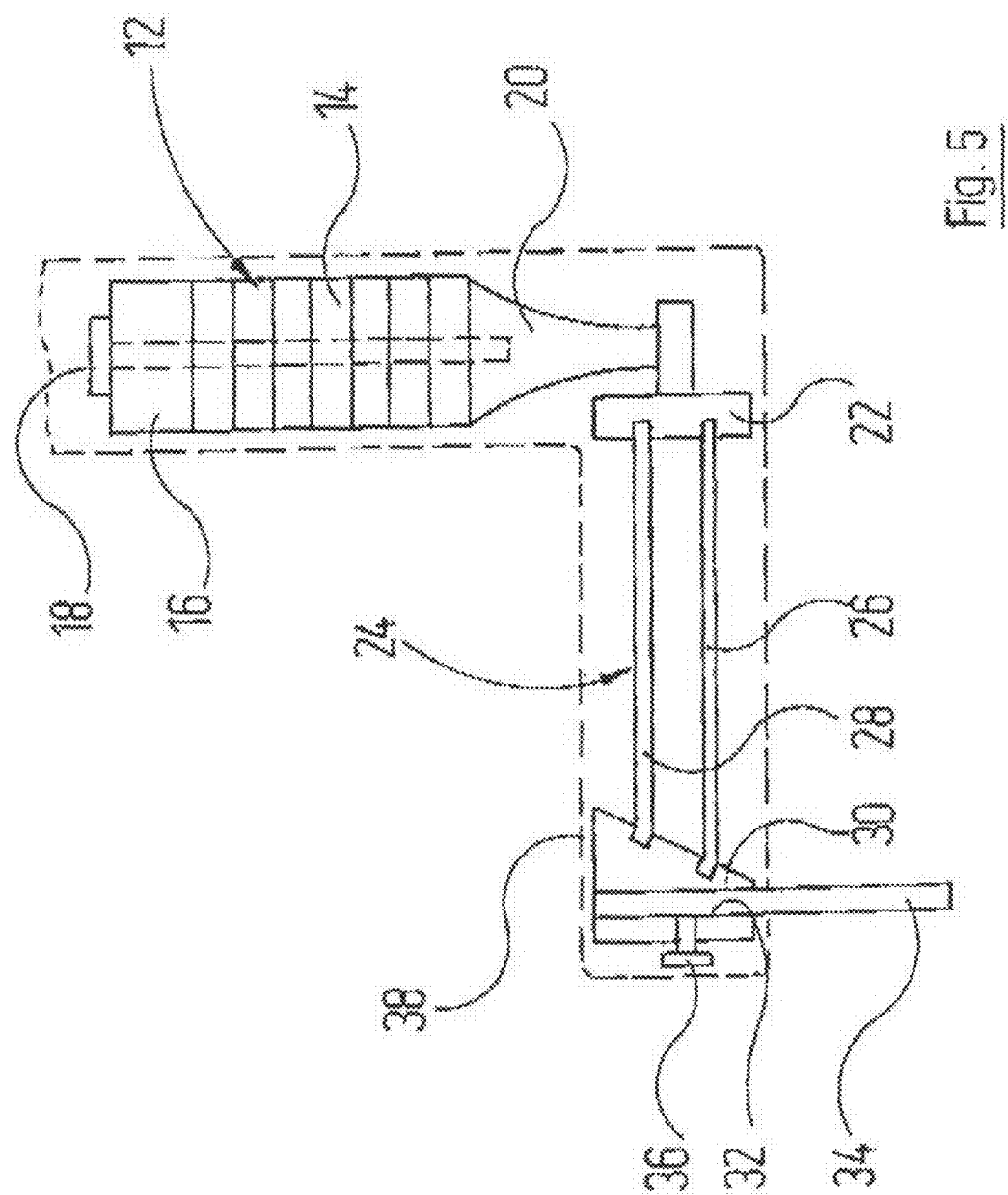
FIG. 5 is a similar view to FIG. 1, but with the coupling unit having vibration bars of different lengths.

FIG. 5 illustrates a variant of the embodiment according to FIG. 1, in which the vibration bar 28 is shorter than the vibration bar 26. The vibration bars 26, 28, the input member 22 and the output member 30 consequently form a trapezoidal vibration system. As described in the embodiments according to FIGS. 3 and 4, the propagation rate for the ultrasound vibration must be selected so as to be different again in the two vibration bars 26, 28 so that the ends of the vibration bars 26, 28 adjacent to the output member 30 each have the same phase position.

Figure 6:
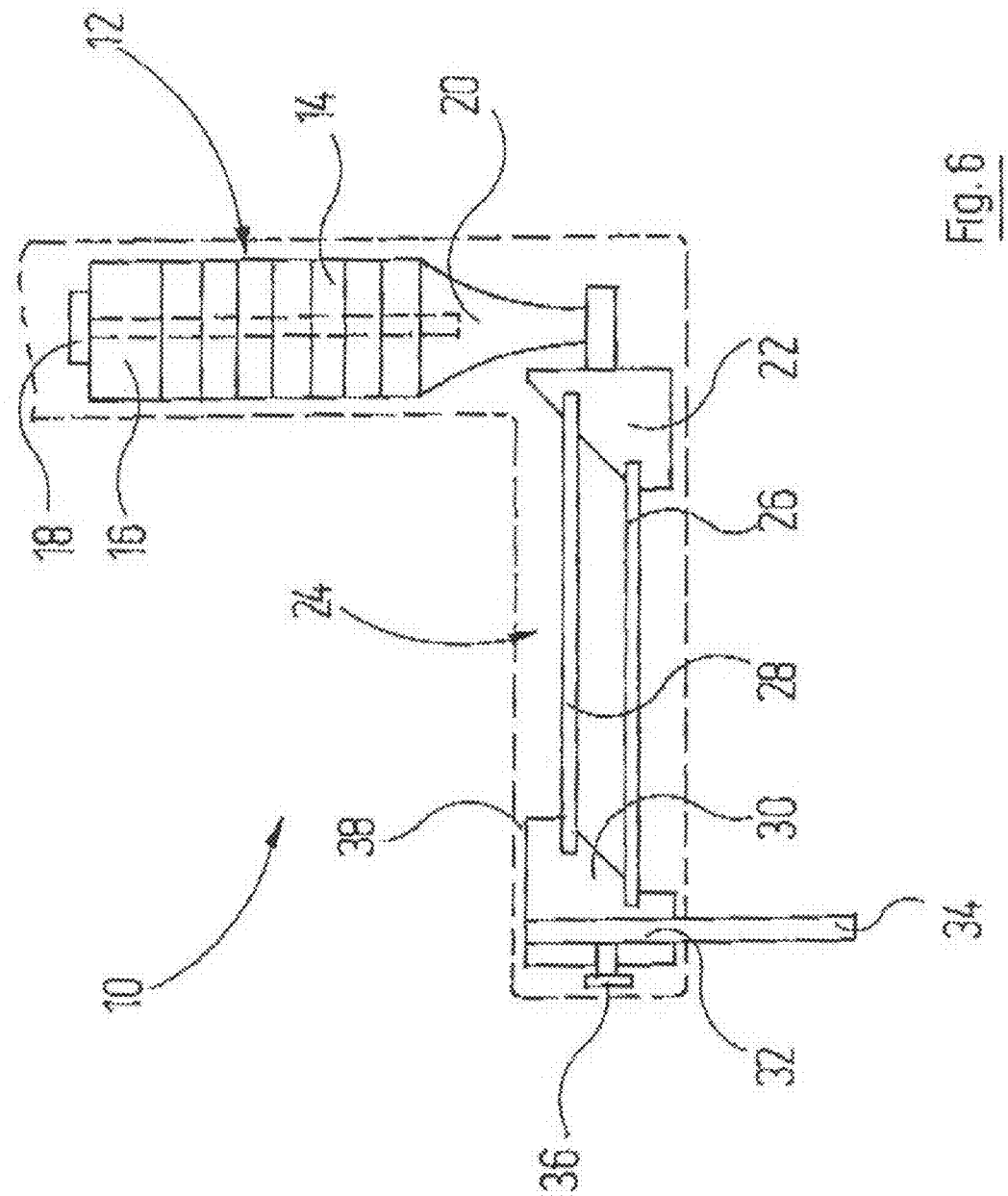
FIG. 6 is a similar view to FIG. 1, but with the vibration bars being part of a parallelogram.

FIG. 6 illustrates a similar variant to FIG. 5, except that the two vibration bars 26, 28 are of the same length and form, together with the input member 22 and output member 30, sides of a parallelogram.

Figure 7:
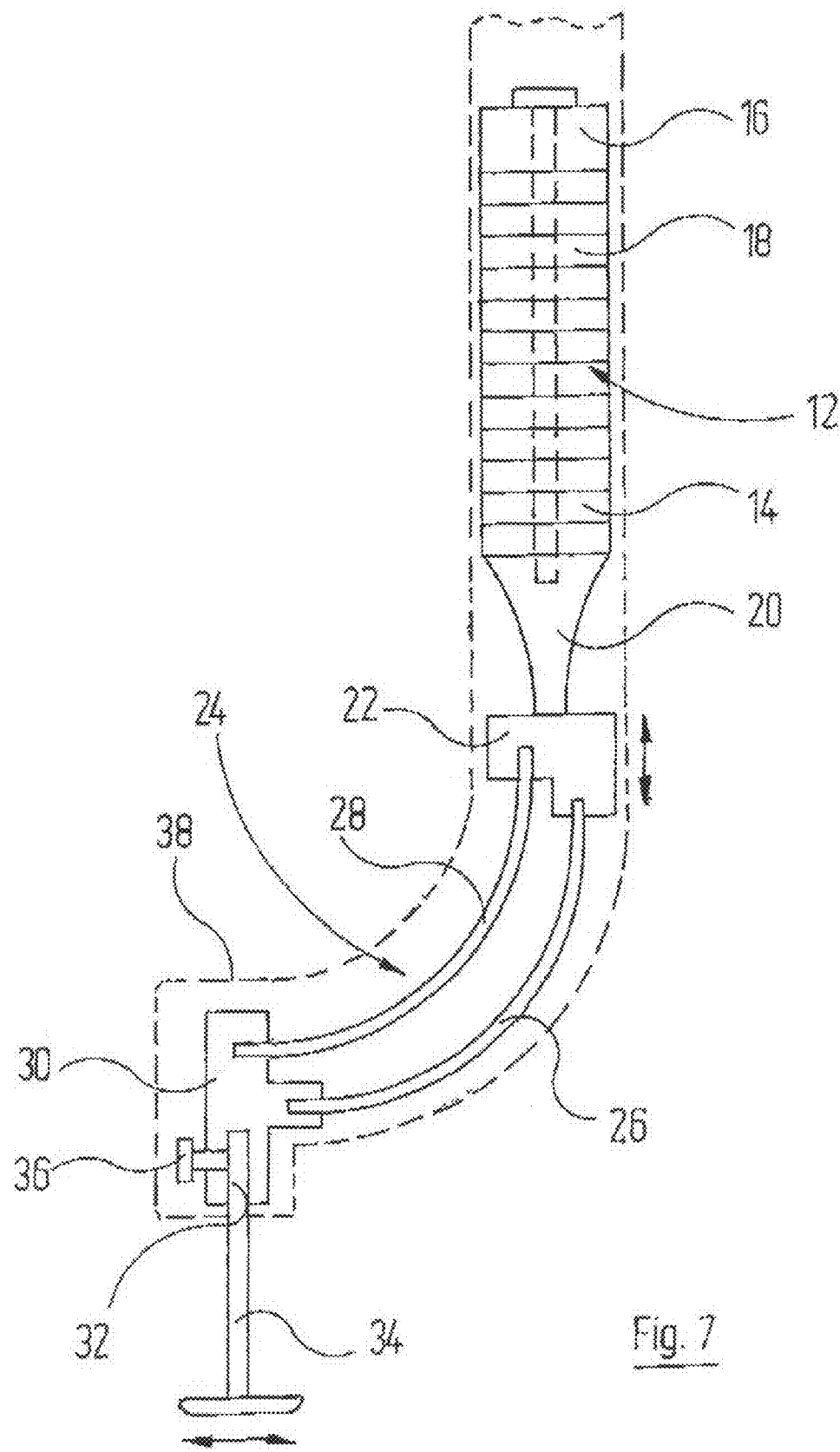
FIG. 7 is a similar view to FIG. 3, but with the operating direction of the vibration generator being turned through 90 degrees.

The embodiment according to FIG. 7 is similar to that according to FIG. 3, except that the axis of the vibration generator is rotated through 90° in the vertical, and the tool 34 carries out a transverse movement which extends parallel with the operating surface of the operating plate thereof.

Figure 8:
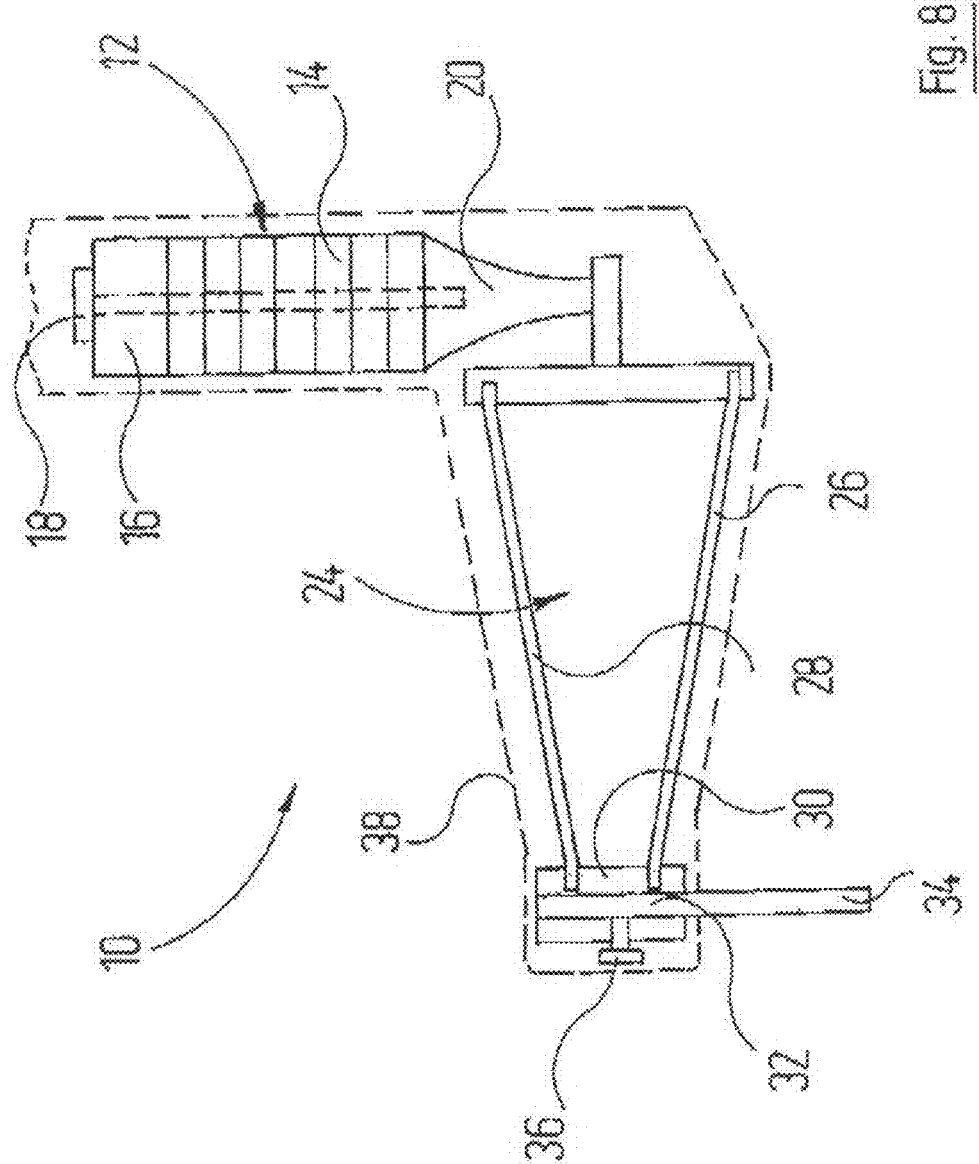
FIG. 8 is a similar view to FIG. 1, but with the vibration bars being part of a cropped triangle or a thin trapezium.

The embodiment according to FIG. 8 is similar to that of FIG. 6, except that the vibration bars 26, 28 are inclined symmetrically relative to a horizontal centre plane of the coupling unit 24 and form, together with the input member 22 and the output member 30, the sides of a cropped triangle or trapezium.

Owing to an increase in the angle of inclination, it is possible, if desired, to achieve cyclical redirection of the output member 30.

Figure 9:
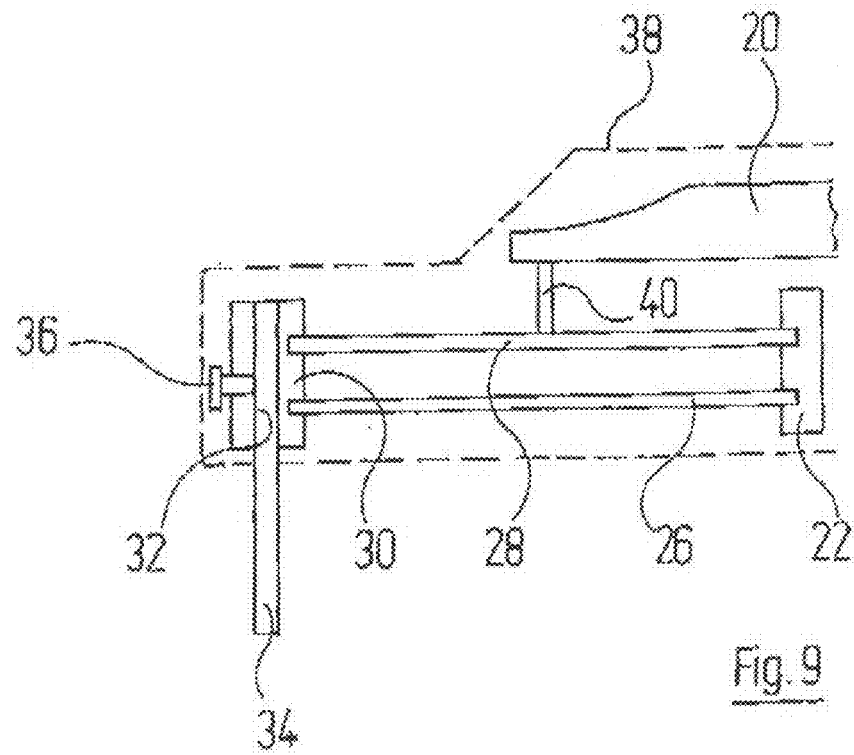
FIG. 9 is a similar view of a coupling unit to that of FIG. 1, but with a drive member operating at the centre of the upper vibration bar.

FIG. 9 illustrates a similar coupling unit to FIG. 1, except with a transversely vibrating sonotrode 20 engaging over a rod-like drive member centrally on the upper vibration bar 26.

Figure 10:
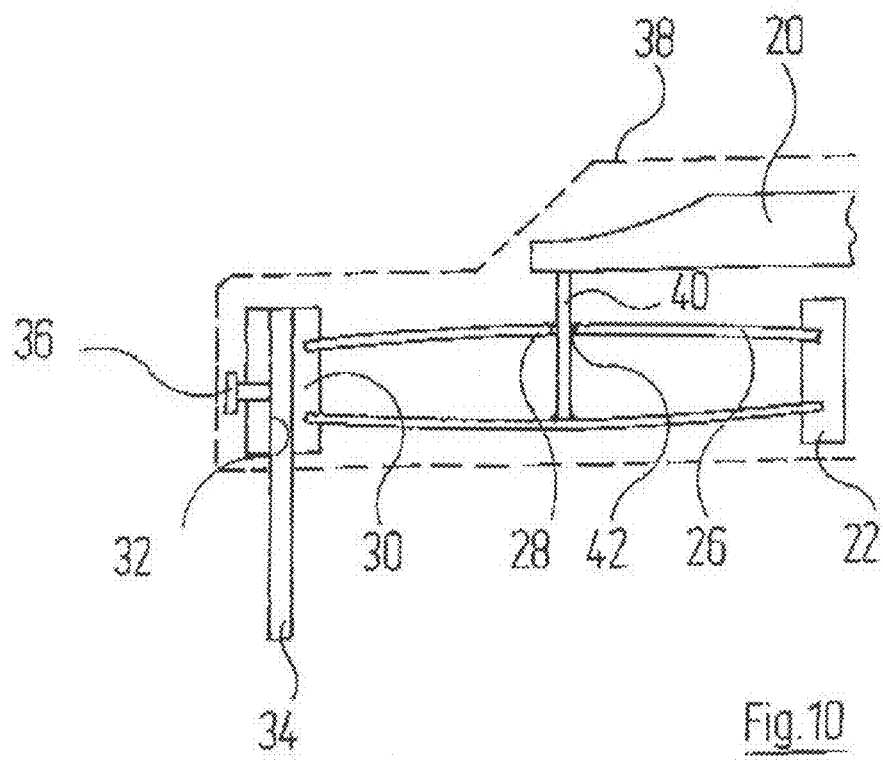
FIG. 10 is a similar view to FIG. 9, but with a drive member operating at the centre of the lower vibration bar.

FIG. 10 corresponds to FIG. 9, except the sonotrode 20 now engages on the lower vibration bar 28, for which reason the drive member 40 is guided with clearance through an opening 42 in the upper vibration bar 26.

Another difference of the coupling unit according to FIG. 10 is that the two vibration bars are curved slightly in the manner of a circular arc in the unloaded state. The radius of the circle is large relative to the length of the vibration bars. Furthermore, the two vibration bars are arranged in a mirror-inverted manner relative to each other so that a biconvex vibration bar arrangement is achieved overall.

In a modification of the embodiment according to FIG. 10, it would also be possible to arrange the two curved vibration bars in a symmetrical manner so that a biconcave vibration bar arrangement is achieved overall.

In another modification of the embodiment according to FIG. 10, it would also be possible to introduce the external force eccentrically in the vibration bar arrangement.

Figure 11:
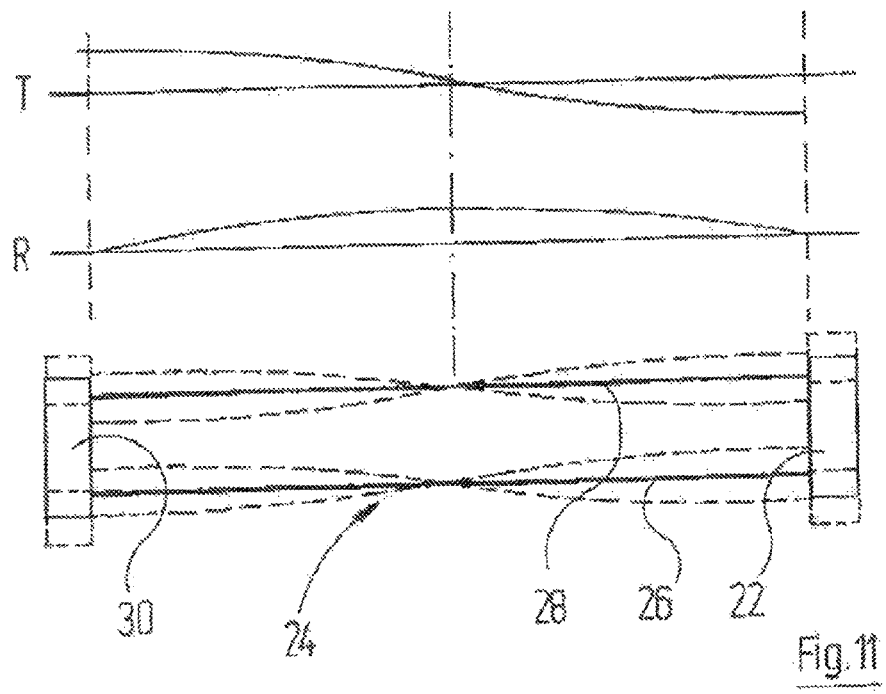
FIG. 11 is a schematic illustration of the vibration shape which is formed in a coupling unit and which comprises two equally long, parallel vibration bars.

FIG. 11 illustrates the vibration shape of a coupling unit 24, as illustrated in FIG. 1, that is to say, a coupling unit having two mutually parallel linear vibration bars 26, 28 of the same length.

In FIG. 11, the vibrations bars 26, 28 are indicated with solid lines in the unloaded state and the positions of greatest deflection from the idle position when the coupling unit 24 vibrates are indicated with broken lines.

It can be seen that the movement of the vibration bars 26, 28 is purely a redirection movement at the centre thereof and, at the ends thereof, purely a translation movement in a direction perpendicular relative to the bar axis. In the points therebetween, the translation movement and redirection movement overlap. The portions of the redirection movement are schematically illustrated in FIG. 11 at R and the portions of the translation movement are illustrated schematically at T.

Figure 12:
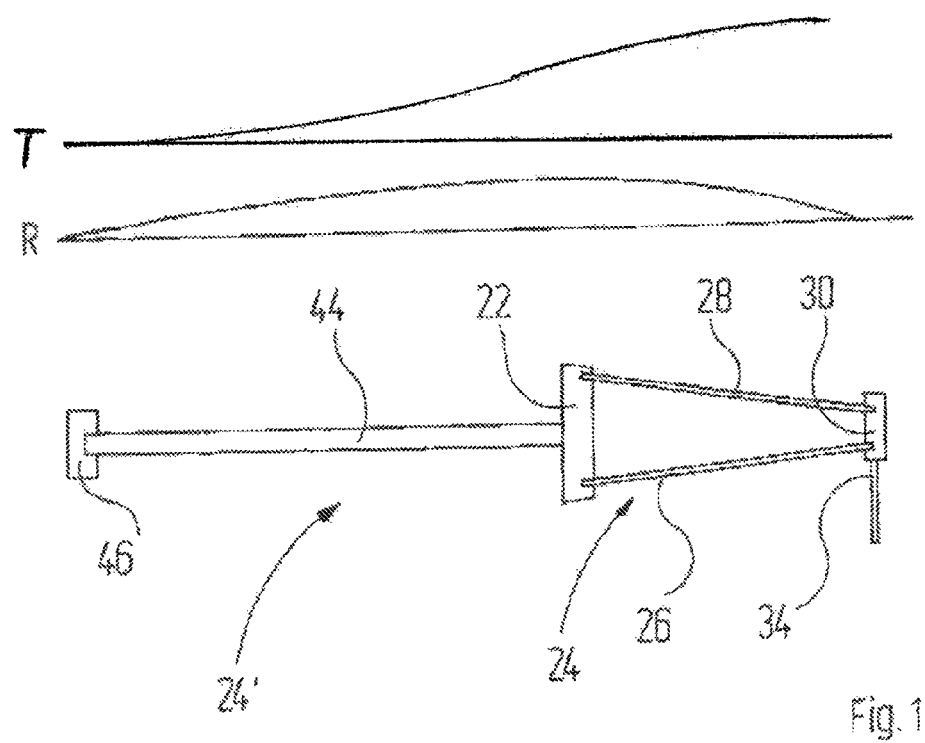
FIG. 12 is a schematic illustration of a coupling unit which is constructed from a series arrangement of an individual vibration bar at one side and two vibration bars which taper towards each other in an inclined manner towards the free end.

FIG. 12 illustrates a modified coupling unit 24' which is formed by a series arrangement comprising a single vibration bar 44 having an input member 46 and a vibration bar arrangement 24 according to FIG. 8.

These two part-systems produce, owing to their construction, opposing redirection movements at the free end. When the two part-systems are configured in an appropriate manner, these two redirection moments may amount to precisely zero, as schematically illustrated in FIG. 12, so that a pure translation movement which is applied to the input member of the coupling unit 24 (input member 46) leads to a pure translation movement of the tool 34.

Titanium is preferred as a material for the vibration bars 26, 28 and preferably also for the input member 22 and the output member 30.

The invention claimed is:

1. A vibration coupling unit for transmitting mechanical vibrations from a high-frequency vibration generator to a tool, having one input member which is driven by ultrasound vibration produced by the high-frequency vibration generator and which is connected to a driving output member by means of a vibration system, wherein the vibration system has at least two vibration bars which extend so as to be mutually spaced-apart and wherein first ends of the vibration bars are connected to the input member and second ends of the vibration bars are connected to the output member.

2. A coupling unit according to claim 1, wherein the vibration bars extend substantially parallel with each other.

3. A coupling unit according to claim 1, wherein the vibration bars have the same geometry and are offset relative to each other.

4. A coupling unit according to claim 3, wherein the vibration bars are orientated in the same manner and the end points thereof define a rectangle.

5. A coupling unit according to claim 1, wherein the vibration bars are linear.

6. A coupling unit according to claim 1, wherein a plurality of vibration systems are connected in series.

7. A coupling unit according to claim 1, wherein the vibration bars have different lengths.

8. A coupling unit according to claim 1, wherein, in the case of a different geometric or material configuration, the vibration bars are constructed in such a manner that vibrations propagate therein at such a different rate that the ends of the vibration bars adjacent to the output member vibrate in phase.

9. A coupling unit according to claim 1, wherein the vibration bars are curved.

10. A coupling unit according to claim 9, wherein tangents at input-side ends of the vibration bars define an angle of approximately from 45° to approximately 135° with tangents at output-side ends of the vibration bars.

11. A coupling unit according to claim 1, wherein the input member and the output member are rigid components compared with the vibration bars.

12. A coupling unit according to claim 1, wherein the input member, at a location remote from the ends of the vibration bars, engages on at least one of the vibration bars.

13. A coupling unit according to claim 12, wherein the input member engages on one of the vibration bars and is guided through an opening in the other of the vibration bars with clearance.

14. A coupling unit according to claim 1, wherein the coupling unit has two vibration bar arrangements which are mechanically connected in series and which in each case superimpose a redirection movement component additionally to a translation movement component of the input movement of the input member, the two vibration bar arrangements being configured in such a manner that the redirection movement components which are produced thereby are mutually emphasized.

15. A coupling unit according to claim 3, wherein the vibration bars are orientated in the same manner and the end points thereof define a parallelogram.

16. A coupling unit according to claim 3, wherein the vibration bars are orientated in the same manner and the end points thereof define a trapezium.

17. A coupling unit according to claim 9, wherein the vibration bars have the shape of a circular arc.

18. A coupling unit according to claim 9, wherein the vibration bars have the shape of an elliptical curve.

19. A coupling unit according to claim 9, wherein the vibration bars have the shape of a hyperbolic curve.

20. A coupling unit according to claim 9, wherein the vibration bars have the shape of a parabolic curve.

21. A coupling unit according to claim 9, wherein tangents at input-side ends of the vibration bars define an angle of approximately 90° with tangents at output-side ends of the vibration bars.

22. A coupling unit according to claim 12, wherein the input member engages on at least one of the vibration bars at the center thereof.

* * * * *